(12) United States Patent
Yoon et al.

(10) Patent No.: US 10,934,400 B2
(45) Date of Patent: Mar. 2, 2021

(54) POROUS SUPER ABSORBENT POLYMER AND PREPARATION METHOD THEREOF

(71) Applicant: LG Chem, Ltd., Seoul (KR)

(72) Inventors: Ki Youl Yoon, Daejeon (KR); Hyo Sook Joo, Daejeon (KR); Gi Cheul Kim, Daejeon (KR); Hyeon Choi, Daejeon (KR); Ju Eun Kim, Daejeon (KR)

(73) Assignee: LG Chem, Ltd.

( * ) Notice: Subject to any disclaimer, the term of this patent is extended or adjusted under 35 U.S.C. 154(b) by 185 days.

(21) Appl. No.: 16/090,966

(22) PCT Filed: Dec. 15, 2017

(86) PCT No.: PCT/KR2017/014874
§ 371 (c)(1),
(2) Date: Oct. 3, 2018

(87) PCT Pub. No.: WO2018/117548
PCT Pub. Date: Jun. 28, 2018

(65) Prior Publication Data
US 2019/0119452 A1    Apr. 25, 2019

(30) Foreign Application Priority Data
Dec. 23, 2016 (KR) .................. 10-2016-0178408

(51) Int. Cl.
| | | |
|---|---|---|
| *C08J 3/075* | (2006.01) | |
| *C08F 20/06* | (2006.01) | |
| *C08K 5/11* | (2006.01) | |
| *C08F 2/26* | (2006.01) | |
| *C08F 2/44* | (2006.01) | |
| *A61L 15/42* | (2006.01) | |
| *C08J 9/00* | (2006.01) | |
| *A61L 15/60* | (2006.01) | |
| *C08F 2/10* | (2006.01) | |
| *C08J 3/24* | (2006.01) | |
| *C08K 3/00* | (2018.01) | |
| *C08K 5/00* | (2006.01) | |
| *C08J 3/12* | (2006.01) | |
| *C07D 317/34* | (2006.01) | |

(Continued)

(52) U.S. Cl.
CPC ............. *C08J 3/075* (2013.01); *A61L 15/425* (2013.01); *A61L 15/60* (2013.01); *B01J 20/267* (2013.01); *B01J 20/28085* (2013.01); *C07D 307/60* (2013.01); *C07D 317/34* (2013.01); *C08F 2/10* (2013.01); *C08F 2/26* (2013.01); *C08F 2/44* (2013.01); *C08F 20/06* (2013.01); *C08F 20/18* (2013.01); *C08F 20/28* (2013.01); *C08J 3/12* (2013.01); *C08J 3/24* (2013.01); *C08J 3/245* (2013.01); *C08J 9/00* (2013.01); *C08K 3/00* (2013.01); *C08K 3/22* (2013.01); *C08K 5/00* (2013.01); *C08K 5/053* (2013.01); *C08K 5/11* (2013.01); *C08K 5/41* (2013.01); *B01J 2220/68* (2013.01); *C08J 2333/02* (2013.01); *C08J 2333/08* (2013.01); *C08J 2333/10* (2013.01); *C08K 3/36* (2013.01); *C08K 2003/2227* (2013.01); *C08K 2201/005* (2013.01)

(58) Field of Classification Search
CPC ....... C08J 3/075; C08J 3/24; C08J 3/12; C08J 3/245; C08J 2333/02; C08J 2333/08; C08J 2333/10; C08J 9/00; C08K 5/11; C08K 3/00; C08K 5/00; C08K 3/22; C08K 5/053; C08K 5/41; C08K 3/36; C08K 2003/2227; C08K 2201/005; C08F 20/06; C08F 2/26; C08F 2/44; C08F 2/10; C08F 20/18; C08F 20/28; A61L 15/425; A61L 15/60; B01J 20/267; B01J 20/28085; B01J 2220/68; C07D 317/34; C07D 307/60
See application file for complete search history.

(56) References Cited

U.S. PATENT DOCUMENTS

| | | |
|---|---|---|
| 5,338,766 A | 8/1994 | Phan et al. |
| 6,107,358 A | 8/2000 | Harada et al. |

(Continued)

FOREIGN PATENT DOCUMENTS

| | | |
|---|---|---|
| CN | 1179433 A | 4/1998 |
| CN | 102317329 A | 1/2012 |

(Continued)

OTHER PUBLICATIONS

Third Party Observation for PCT/KR2017/014874 dated Apr. 22, 2019.

(Continued)

*Primary Examiner* — Patrick D Niland
(74) *Attorney, Agent, or Firm* — Lerner, David, Littenberg, Krumholz & Mentlik, LLP

(57) ABSTRACT

The present disclosure relates to a preparation method of a porous super absorbent polymer exhibiting excellent absorption performance and improved absorption rate due to a novel pore structure, and a porous super absorbent polymer prepared therefrom. The porous super absorbent polymer includes a base resin powder including a cross-linked polymer of a water soluble ethylene-based unsaturated monomer containing acidic groups which are at least partially neutralized, and an inorganic filler contained in the cross-linked structure of the cross-linked polymer, wherein the base resin powder includes a plurality of pores having a diameter of a sub-micron (sub-μm) scale in the cross-linked structure, and an interconnected pore structure in the form of an open channel in which 90% or more of the pores are connected to each other.

15 Claims, 2 Drawing Sheets

(51) Int. Cl.
*C07D 307/60* (2006.01)
*B01J 20/26* (2006.01)
*B01J 20/28* (2006.01)
*C08F 20/18* (2006.01)
*C08F 20/28* (2006.01)
*C08K 3/22* (2006.01)
*C08K 5/053* (2006.01)
*C08K 5/41* (2006.01)
*C08K 3/36* (2006.01)

(56) References Cited

U.S. PATENT DOCUMENTS

| | | | |
|---|---|---|---|
| 6,136,873 | A | 10/2000 | Hahnle et al. |
| 6,174,929 | B1 | 1/2001 | Hahnle et al. |
| 2004/0110913 | A1 | 6/2004 | Kanto et al. |
| 2010/0331802 | A1 | 12/2010 | Yokoyama et al. |
| 2011/0313113 | A1 | 12/2011 | Sakamoto et al. |
| 2012/0232177 | A1 | 9/2012 | Lopez Villanueva et al. |
| 2013/0101851 | A1 | 4/2013 | Takaai et al. |
| 2015/0004127 | A1 | 1/2015 | Ishimori et al. |
| 2017/0014801 | A1 | 1/2017 | Ikeuchi et al. |

FOREIGN PATENT DOCUMENTS

| | | | |
|---|---|---|---|
| CN | 104080814 | A | 10/2014 |
| CN | 104231144 | A | 12/2014 |
| EP | 0827753 | A2 | 3/1998 |
| EP | 2088160 | A1 | 8/2009 |
| EP | 2399944 | A1 | 12/2011 |
| EP | 2518092 | A1 | 10/2012 |
| EP | 2565219 | A1 | 3/2013 |
| EP | 2589613 | A1 | 5/2013 |
| EP | 2612886 | A1 | 7/2013 |
| EP | 1837348 | B1 | 9/2013 |
| JP | H08508527 | A | 9/1996 |
| JP | 2881739 | B2 | 4/1999 |
| JP | H11514691 | A | 12/1999 |
| JP | 2005126474 | A | 5/2005 |
| JP | 2006342306 | A | 12/2006 |
| JP | 2009203383 | A | 9/2009 |
| JP | 2015174971 | A | 10/2015 |
| JP | 2015199958 | A | 11/2015 |
| JP | 2016016667 | A | 2/2016 |
| KR | 19990027352 | A | 5/2000 |
| KR | 20030078925 | A | 10/2003 |
| KR | 20050022813 | A | 3/2005 |
| KR | 20140147124 | A | 12/2014 |
| KR | 1020160127742 | A | 11/2016 |
| WO | 9422502 | A1 | 10/1994 |
| WO | 9851408 | A1 | 11/1998 |
| WO | 9900187 | A1 | 1/1999 |
| WO | 2007103208 | A2 | 9/2007 |
| WO | 2012002455 | A1 | 1/2012 |

OTHER PUBLICATIONS

Extended European Search Report including Written Opinion for Application No. EP17883843 dated Feb. 25, 2019.
International Search Report for Application No. PCT/KR2017/014874, dated Apr. 9, 2018.
Odian, George, "Principles of Polymerization", John Wiley & Sons, 1981, p. 203.
Schwalm, Reinhold, "UV Coatings: Basics, Recent Developments and New Applications", Elsevier, Dec. 2006, 3 pages.
Chinese Search Report for Application No. 201780022806.2, dated Aug. 3, 2020, pp. 1-3.

[Fig. 1]
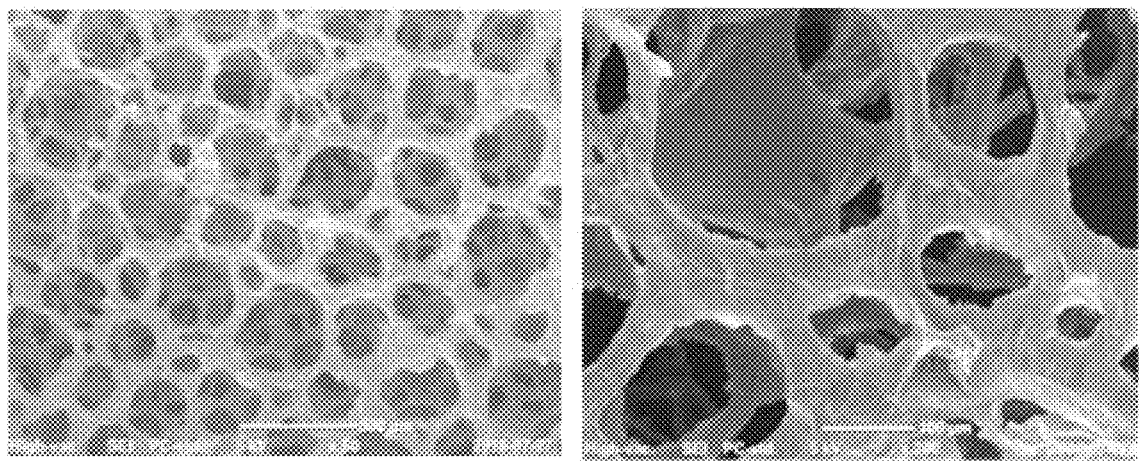
[Fig. 2]
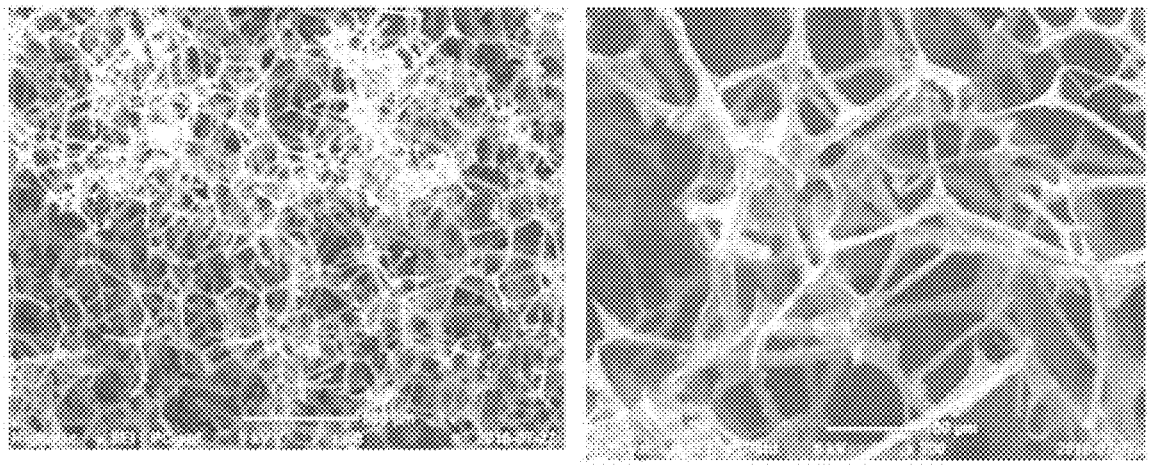

[Fig. 3]
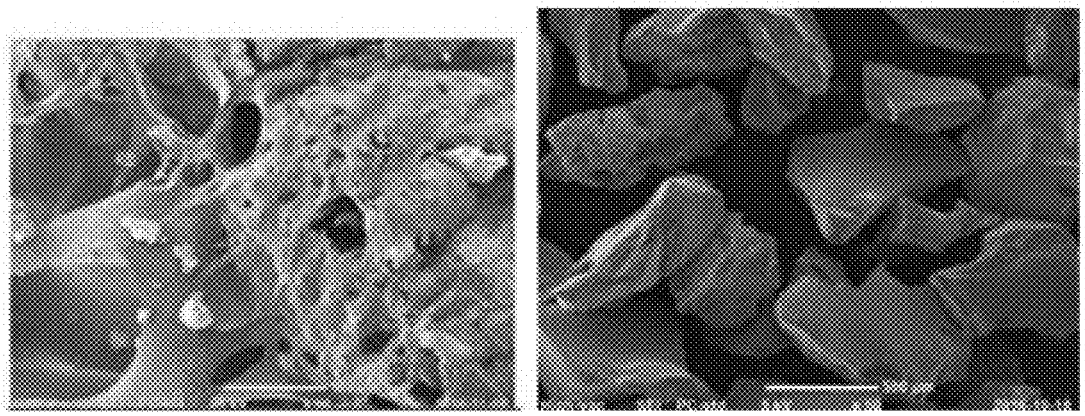
[Fig. 4]
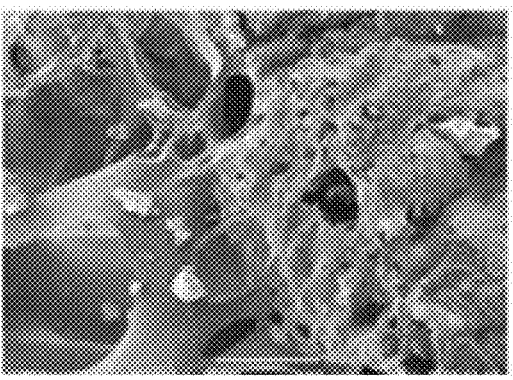
[Fig. 5]
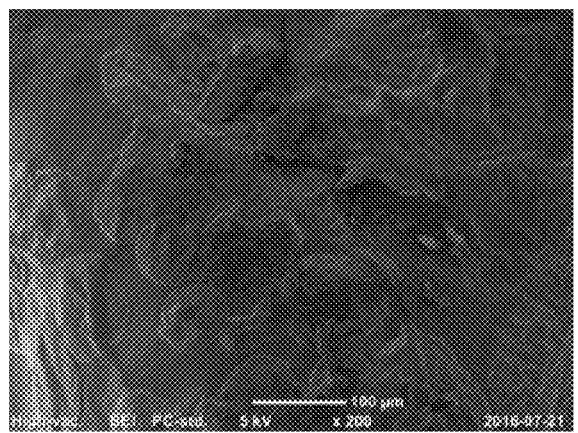

POROUS SUPER ABSORBENT POLYMER AND PREPARATION METHOD THEREOF

CROSS-REFERENCE TO RELATED APPLICATIONS

This application is a national phase entry under 35 U.S.C. § 371 of International Application No. PCT/KR2017/014874, filed Dec. 15, 2017, which claims priority to Korean Patent Application No. 10-2016-0178408, filed Dec. 23, 2016, the disclosures of which are incorporated herein by reference.

TECHNICAL FIELD

The present disclosure relates to a preparation method of a porous super absorbent polymer exhibiting excellent absorption performance and improved absorption rate due to a novel pore structure, and a porous super absorbent polymer prepared therefrom.

BACKGROUND OF ART

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, sanitary napkins, etc., but also for water retaining soil products for gardening, water stop materials for the civil engineering and construction, sheets for raising seedling, fresh-keeping agents for food distribution fields, materials for poultices, or the like.

In most cases, the super absorbent polymer is widely used in the field of hygiene products such as diapers and sanitary napkins, and, for this purpose, it is necessary to exhibit basic absorption performance such as high absorption capacity and water retention capacity for moisture. In addition, recently, in order to further reduce discomfort of hygiene users, there is a continuing demand for providing a super absorbent polymer exhibiting high absorption rate.

A typical method for improving the absorption rate of the super absorbent polymer is to provide a porous super absorbent polymer containing a large number of micropores in the super absorbent polymer. Previously, in order to provide such a porous super absorbent polymer, a foaming agent was used, or an artificial foaming method by injecting gas was applied in the polymerization process for preparing a super absorbent polymer.

However, the porous super absorbent polymer prepared by this conventional method has a limitation in increasing its porosity. In addition, it is a fact that a plurality of pores in the polymer are formed independently from each other, which has a limitation in improving the absorption rate.

Therefore, there is a continuing demand to develop a technique that maintain the basic absorption performance of the super absorbent polymer while improving the absorption rate of the super absorbent polymer compared with the previously known methods.

DETAILED DESCRIPTION OF THE INVENTION

Technical Problem

Thus, the present disclosure is to provide a method for preparing a porous super absorbent polymer exhibiting improved absorption rate while maintaining excellent basic absorption performance such as water retention capacity due to a novel pore structure, and a porous super absorbent polymer prepared therefrom.

Technical Solution

The present disclosure provides a preparation method of a porous super absorbent polymer, including the steps of:
preparing a monomer composition comprising a water soluble ethylene-based unsaturated monomer containing acidic groups which are at least partially neutralized, an internal cross-linking agent, an initiator, an inorganic filler, and an anionic surfactant;
stirring the monomer composition under a shear force at a rate of 3000 to 20,000 rpm to generate bubbles in the monomer composition;
preparing a hydrogel polymer by cross-linking the monomer composition; and
preparing a base resin powder by drying, pulverizing, and classifying the hydrogel polymer,
wherein the monomer has acidic groups which are at least 80 mol % neutralized, and
the anionic surfactant has 10 or more carbon atoms or HLB of 15 or more, and includes a compound in the form of a sulfate salt, a carboxylate salt or a phosphate salt.

The present disclosure also provides a porous super absorbent polymer, including a base resin powder including a cross-linked polymer of a water soluble ethylene-based unsaturated monomer containing acidic groups which are at least partially neutralized, and an inorganic filler contained in the cross-linked structure of the cross-linked polymer,
wherein the base resin powder includes a plurality of pores having a diameter of a sub-micron (sub-µm) scale in the cross-linked structure, and an interconnected pore structure in the form of an open channel in which 90% or more of the pores are connected to each other.

Hereinafter, the porous super absorbent polymer and its preparation method according to the exemplary embodiments of the present disclosure will be described in more detail. However, the following is only for better understanding of the present invention, and the scope of the present invention is not limited thereby, and it is obvious to a person skilled in the related art that the embodiments can be variously modified within the scope of the present invention.

The term "include" or "have" means to include any elements (or components) without particular limitation unless there is a particular mention about them in this description, and it cannot be interpreted as having a meaning of excluding addition of other elements (or components).

In this disclosure, (meth) acrylate is meant to include both acrylate and methacrylate.

And, in this disclosure, a micron (µm) scale refers to having a maximum diameter of less than 1 mm, that is, less than 1000 µm, a nano (nm) scale refers to having a maximum diameter of less than 1 µm, that is, less than 1000 nm, and a sub-micron (sub-µm) scale refers to having a maximum diameter of a micron scale or nano scale.

In this disclosure, when diameter values of any cross-section of the pores are measured, the "maximum diameter" of the pores may refer to the maximum value of these diameters.

One embodiment of the present disclosure provides a preparation method of a porous super absorbent polymer, including the steps of:
preparing a monomer composition comprising a water soluble ethylene-based unsaturated monomer containing acidic groups which are at least partially neutralized, an internal cross-linking agent, an initiator, an inorganic filler, and an anionic surfactant;

stirring the monomer composition under a shear force at a rate of 3000 to 20,000 rpm to generate bubbles in the monomer composition;

preparing a hydrogel polymer by cross-linking the monomer composition; and preparing a base resin powder by drying, pulverizing, and classifying the hydrogel polymer, wherein the monomer has acidic groups which are at least 80 mol % neutralized, and the anionic surfactant has 10 or more carbon atoms or HLB of 15 or more, and includes a compound in the form of a sulfate salt, a carboxylate salt or a phosphate salt.

In the preparation method of one embodiment, a specific anionic surfactant and an inorganic filler are used in the polymerization process for preparing a super absorbent polymer, and the polymerization is carried out after neutralizing the unsaturated monomer by a high neutralization degree of 80 mol % or more. In addition, in the method of one embodiment, a plurality of pores are generated due to an interaction between the anionic surfactant and the inorganic filler by applying a shear force to the monomer composition satisfying the above requirements and stirring at a constant rate. The monomer composition was subjected to a subsequent process such as cross-linking polymerization to prepare a porous super absorbent polymer.

As a result of continuing experiments conducted by the present inventors, it has been confirmed that the preparation method of this embodiment can provide a porous super absorbent polymer having porosity much higher than that of previously known polymers, and a novel pore structure. As will be described in more detail below, it has been confirmed that the porous super absorbent polymer obtained by the above method has an interconnected pore structure in the form of an open channel in which a plurality of pores, for example, 90% or more, or 90 to 100% of the pores are connected each other, and high porosity such that the base resin powder has a pore volume fraction of 0.74 or more, or 0.75 to 0.9, defined as a ratio of the volume of the plurality of pores to the total volume.

For reference, when observing the pore structure inside the porous super absorbent polymer using a scanning electron microscope (SEM; magnification: ×50 or ×200), the interconnected pore structure in which a plurality of pores have an open channel shape can be confirmed. Also, by confirming the pore structure, it can be confirmed that the pore volume fraction satisfies the high range of 0.74 or more. It may be presumed that its technical principle is similar to that of the interconnected pore structure in the porous polymer prepared by a high internal phase emulsion (HIPE) method. And, the formation of the pore structure makes it possible to satisfy the above-described high pore volume fraction and the open channel form.

Due to the novel pore structure and high porosity, the porous super absorbent polymer can exhibit higher absorption rate than previously known, and it has been confirmed that the basic absorption performance, such as water retention capacity, is also excellent.

The reason why the novel pore structure and the high porosity can be obtained by the preparation method of the embodiment is expected that the specific anionic surfactant and the inorganic filler interact in the polymerization process to form more uniform bubbles/pores, and particularly, a large number of bubbles can be formed under a specific stirring condition. In addition, it is also because the high neutralization degree of the monomer stabilizes the large number of uniform bubbles/pores, and the interconnected pore structure can stably maintain, so that the pore structure can maintain in the finally prepared super absorbent polymer.

Accordingly, the method of one embodiment makes it possible to provide a porous super absorbent polymer exhibiting higher absorption rate and excellent absorption performance, and thus can be preferably applied to various sanitary materials.

Hereinafter, the preparation method of one embodiment will be described in more detail step by step.

In the preparation method of the above-described embodiment, the water soluble ethylene-based unsaturated monomer may be any unsaturated monomer previously known to be usable for the preparation of super absorbent polymers. For example, an anionic monomer of acrylic acid, methacrylic acid, maleic anhydride, fumalic acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid may be used without particular limitations, and at least 80 mol % or more, or 80 mol % to 95 mol % of the acidic groups contained in the monomer may be neutralized with a basic compound such as sodium hydroxide. That is, the monomer may be used in a state including the unsaturated monomer described above and a salt in which the acidic groups thereof are at least 80 mol % neutralized.

As described above, by controlling the neutralization degree of the monomer to 80 mol % or more, high porosity and the novel pore structure can be more stably and effectively obtained in the finally formed porous super absorbent polymer.

The neutralization degree of the water soluble ethylene-based unsaturated monomer containing acidic groups can be calculated and confirmed from a molar ratio of the acidic groups of the used unsaturated monomer to the hydroxyl groups of the basic compound.

And, the monomer composition includes an internal cross-linking agent for introducing a basic cross-linking structure into the base resin powder together with the monomer. As the internal cross-linking agent, any internal cross-linking agent having a cross-linkable functional group used in the preparation of a super absorbent polymer can be used without any limitation. However, a multifunctional (meth)acrylate-based compound having a plurality of ethylene oxide groups may be suitably used as the internal cross-linking agent in order to improve physical properties of the super absorbent polymer by introducing an appropriate cross-linking structure into the base resin powder.

Specific examples of the internal cross-linking agent include at least one selected from the group consisting of polyethylene glycol diacrylate (PEGDA), glycerine diacrylate, glycerine triacrylate, unmodified or ethoxylated trimethylol triacrylate (TMPTA), hexanediol diacrylate, and triethylene glycol diacrylate.

The internal cross-linking agent may be used in an amount of about 0.1 parts by weight or more, about 0.15 parts by weight or more, or about 0.15 to 0.6 parts by weight based on 100 parts by weight of the unsaturated monomer in an un-neutralized state. By using the internal cross-linking agent within the range, an appropriate cross-linking structure is introduced into the base resin powder and the super absorbent polymer, thereby improving the absorption performance such as absorption ability under pressure.

Meanwhile, the monomer composition may further include an anionic surfactant and an inorganic filler for forming a plurality of bubbles in the monomer composition and exhibiting the porosity of the super absorbent polymer.

The anionic surfactant, particularly, may have 10 or more carbon atoms, or HLB of 15 or more, and may be a compound in the form of a sulfate salt, a carboxylate salt or a phosphate salt. It has been confirmed that the use of the specific anionic surfactant effectively forms a new pore structure and a high porosity in the super absorbent polymer to achieve higher absorption rate of the super absorbent polymer. On the other hand, when an anionic surfactant having smaller carbon atoms and a lower HLB value is used, the new pore structure and the high porosity may not be achieved properly.

Specific examples of the anionic surfactant may include sodium dodecyl sulfate, sodium dodecanoate, alkyl phosphate having a C10 to C30 alkyl group, alkyl sulfate having a C10 to C30 alkyl group, or alkyl carboxylate having a C10 to C30 alkyl group. This anionic surfactant may have a HLB value of 15 or more, 15 to 50, or 20 to 40. In addition, the anionic surfactant may have a number average molecular weight of 220 to 800. As the anionic surfactant satisfies the above-described characteristics, the above-described pore structure can be formed more effectively.

The above-described anionic surfactant can be obtained by using commercially available surfactants, or they can be directly synthesized by a method well known to those skilled in the art.

The anionic surfactant may be used in an amount of 0.1 to 5 parts by weight, or 0.5 to 3 parts by weight, based on 100 parts by weight of the unsaturated monomer. As a result, the above-described pore structure can be formed more effectively, and a base resin powder and a super absorbent polymer having an appropriate cross-linking structure can be prepared.

Meanwhile, the above-described inorganic filler is a component that assists in formation of a proper pore structure in the super absorbent polymer together with the anionic surfactant, particularly, assists in formation of a pore structure in the form of an open channel in which a plurality of pores are connected to each other.

This inorganic filler may be a silica nanoparticle, a cellulose-based nanocrystal, or an alumina nanoparticle. For example, it may have a diameter of 5 to 400 nm. This allows the plurality of pores to be connected more effectively and a pore structure in the form of an open channel can be appropriately formed.

The content of the inorganic filler may vary depending on the shape and characteristics of the finally prepared porous super absorbent polymer. For example, the inorganic filler may be used in an amount of 0.1 to 20 parts by weight, or 0.5 to 10 parts by weight, based on 100 parts by weight of the unsaturated monomer. By using the inorganic filler in an appropriate content range, it is possible to effectively form the pore structure in the super absorbent polymer and to control the porosity of the super absorbent polymer by controlling the pore size.

Meanwhile, the monomer composition may further include a thermal polymerization initiator or a photopolymerization initiator. The polymerization initiator may be an initiator for thermal polymerization or an initiator for photopolymerization by UV radiation according to the polymerization method. However, even when the photopolymerization method is applied thereto, a certain amount heat is generated by UV radiation and the like, and some heat occurs as the polymerization reaction, an exothermal reaction, progresses. Therefore, the composition may additionally include the thermal polymerization initiator.

Here, any compound which can form a radical by light such as UV rays may be used as the photopolymerization initiator without limitation.

For example, the photopolymerization initiator may be one or more compounds selected from the group consisting of benzoin ether, dialkyl acetophenone, hydroxyl alkylketone, phenyl glyoxylate, benzyl dimethyl ketal, acyl phosphine, and α-aminoketone. Further, as the specific example of acyl phosphine, commercial Lucirin TPO, namely, 2,4,6-trimethyl-benzoyl-trimethyl phosphine oxide, may be used. More various photopolymerization initiators are well disclosed in "UV Coatings: Basics, Recent Developments and New Application (Elsevier, 2007)" written by Reinhold Schwalm, p 115, and the present invention is not limited thereto.

The concentration of the photopolymerization initiator in the monomer composition may be about 0.01 to about 1.0 wt %. When the concentration of the photopolymerization initiator is excessively low, the polymerization rate becomes slow, and when the concentration of the photopolymerization initiator is excessively high, the molecular weight of the super absorbent polymer becomes low and the properties may be uneven.

Furthermore, as the thermal polymerization initiator, one or more initiators selected from the group consisting of a persulfate-based initiator, an azo-based initiator, hydrogen peroxide, and ascorbic acid may be used. Specifically, sodium persulfate ($Na_2S_2O_8$), potassium persulfate ($K_2S_2O_8$), ammonium persulfate (($NH_4)_2S_2O_8$), and the like may be used as examples of the persulfate-based initiators; and 2,2-azobis-(2-amidinopropane)dihydrochloride, 2,2-azobis-(N,N-dimethylene)isobutyramidinedihydrochloride, 2-(carbamoylazo)isobutylonitril, 2,2-azobis-[2-(2-imidazolin-2-yl)propane]dihydrochloride, 4,4-azobis-(4-cyanovaleric acid), and the like may be used as examples of azo-based initiators. More various thermal polymerization initiators are well disclosed in "Principle of Polymerization (Wiley, 1981)" written by Odian, p 203, and the present invention is not limited thereto.

The concentration of the thermal polymerization initiator included in the monomer composition may be about 0.001 to about 0.5 wt %. When the concentration of the thermal polymerization initiator is excessively low, additional thermal polymerization hardly occurs and there may be less effect according to the addition of the thermal polymerization initiator, and when the concentration of the thermal polymerization initiator is excessively high, the molecular weight of the super absorbent polymer becomes low and the properties may be uneven.

Furthermore, the monomer composition may further include an additive such as a thickener, a plasticizer, a preservation stabilizer, an antioxidant, and the like, if necessary.

The monomer composition may be prepared in a solution state in which the above-described components are dissolved in a solvent.

At this time, any solvent which can dissolve or disperse the components may be used without limitation, and for example, one or more solvents selected from water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butyrolactone, carbitol, methylcellosolve acetate, N,N-dimethylacetamide, and the like may be used solely or in combination.

The solvent may be included in the monomer composition at a residual quantity except for the above components.

Meanwhile, the amount of the water soluble ethylene-based unsaturated monomer in the monomer composition may be about 20 to about 60 wt %, or about 40 to 50 wt %, and a proper concentration may be selected by considering polymerization time and reaction conditions. However, when the concentration of the monomer is excessively low, there may be a problem in economy because the yield of the super absorbent polymer becomes low, and contrarily, when the concentration is excessively high, there may be a problem in the process in that part of the monomer is extracted or the pulverizing efficiency becomes low in the pulverization process of the polymerized hydrogel polymer, and the properties of the super absorbent polymer may decrease.

After the above-described monomer composition is formed, bubbles can be generated in the monomer composition by stirring the same under a shear force. As described above, the bubbles are generated due to the action of the anionic surfactant and the inorganic filler by the stirring under the shear force, and these bubbles can be stabilized by the high neutralization degree. Thus, when the subsequent polymerization proceeds, a super absorbent polymer having the above-described pore structure or the like can be prepared by such bubbles.

This stirring step under the shear force may be carried out by applying conventionally known apparatuses and mixing methods in the step of high-shear mixing.

For example, examples of the apparatuses that can be used in the stirring step include a microfludizer, a fil mixer, a planetary dispersive mixer, a mechanical mixer, or a homogenizer.

The stirring step may include a step of mixing the monomer composition at a rate of 3000 to 20,000 rpm, or 3500 to 10,000 rpm. This allows the formation of bubbles in an appropriate level, and a super absorbent polymer exhibiting a novel pore structure and improved absorption rate can be suitably prepared.

The duration time of the step of stirring the monomer composition is not particularly limited, but can be carried out for 1 min to 100 min, or 10 min to 60 min. If the duration time for carrying out the stirring is too short, the formation of bubbles in the composition is insufficient so that the pore structure in the super absorbent polymer may not be formed properly.

After the bubbles are generated by stirring the monomer composition under a shear force, a hydrogel polymer may be prepared by cross-linking the monomer composition. The cross-linking polymerization step may be carried out by thermal polymerization or photopolymerization.

This polymerization may be carried out according to a conventional polymerization method and conditions for preparing a general super absorbent polymer.

Specifically, the polymerization method is largely divided into the thermal polymerization and the photopolymerization according to the energy source of the polymerization. In the case of thermal polymerization, it is generally carried out in a reactor having a kneading spindle, such as a kneader. In the case of photopolymerization, it may be carried out in a reactor equipped with a movable conveyor belt.

For example, as described above, the hydrogel polymer obtained by carrying out the thermal polymerization by providing hot air to a reactor equipped with a kneading spindle such as a kneader or heating the reactor is discharged from the outlet of the reactor and may have a size of centimeters or millimeters, according to the shape of the kneading spindle installed in the reactor. Specifically, the size of the obtained hydrogel polymer may vary according to the concentration and the feeding rate of the monomer composition, and generally the obtained hydrogel polymer may have a weight average diameter of about 2 to about 50 mm.

Furthermore, in the case of carrying out the photopolymerization in a reactor equipped with a movable conveyor belt, the hydrogel polymer may be obtained in the form of a sheet having a width corresponding to a width of the belt. At this time, the thickness of the polymer sheet may vary according to the concentration and the feeding rate of the monomer composition, but it is preferable to feed the monomer composition so that a polymer sheet having a thickness of about 0.5 to about 5 cm can be obtained. It is undesirable to feed the monomer composition so that the thickness of the polymer sheet becomes excessively thin, because it makes the production efficiency low, and if the thickness of the obtained polymer sheet is over 5 cm, the polymerization reaction cannot evenly occur across the thickness because of its excessively thick thickness.

Generally, the moisture content of the hydrogel polymer obtained by the above method may be about 40 to about 80 wt %. At this time, the "moisture content" is the content of moisture in the entire weight of the hydrogel polymer, and it means a value of which the weight of the dried polymer is subtracted from the weight of the hydrogel polymer. Specifically, the moisture content is defined as a value calculated from the weight loss due to moisture evaporation from the polymer in the process of increasing the temperature of the polymer and drying the same through infrared heating. At this time, the drying condition for measuring the moisture content is that the temperature is increased to about 180° C. and maintained at 180° C., and the total drying time is 20 min including 5 min of a heating step.

Further, after the cross-linking polymerization of the monomer, the base resin powder may be obtained by the processes of drying, pulverization, classification, and the like. Here, it is preferable that the base resin powder and the super absorbent polymer obtained therefrom are prepared and provided so as to have a diameter of about 150 to 850 μm, through the processes of pulverization and classification. More specifically, at least about 95 wt % of the base resin powder and the super absorbent polymer obtained therefrom have a diameter of about 150 to 850 μm, and the fine powder having a diameter less than about 150 μm may be less than about 3 wt %.

Since the particle size distributions of the base resin powder and the super absorbent polymer are controlled in a preferable range, the finally prepared super absorbent polymer can exhibit better absorption performance and the like.

The processes of drying, pulverization, and classification will be described in more detail as follows.

First, in drying the hydrogel polymer, a coarse pulverizing step may be further included before the drying step for increasing the drying efficiency, if necessary.

Here, the pulverizing machine is not particularly limited. Specifically, it may include at least one selected from the group consisting of a vertical pulverizer, a turbo cutter, a turbo grinder, a rotary cutter mill, a cutter mill, a disc mill, a shred crusher, a crusher, a chopper, and a disc cutter, but it is not limited thereto.

In the coarse pulverizing step, the hydrogel polymer may be crushed to have a diameter of about 2 to about 10 mm.

It is technically difficult to pulverize the hydrogel polymer to have a diameter of less than 2 mm because of its high moisture content, and there may be a phenomenon that the crushed particles cohere with each other. Meanwhile, when the polymer is crushed to have a diameter of larger than 10 mm, the efficiency enhancing effect in the subsequent drying step may be low.

The hydrogel polymer coarsely pulverized as above or the hydrogel polymer immediately after the polymerization without the coarse pulverizing step is subjected to drying. At this time, the drying temperature of the drying step may be about 150 to about 250° C. When the drying temperature is lower than about 150° C., the drying time may become excessively long and the properties of the super absorbent polymer finally prepared may decrease. And when the drying temperature is higher than about 250° C., the surface of the polymer is excessively dried, and fine powders may be generated in the subsequent pulverization process and the properties of the super absorbent polymer finally prepared may decrease. Therefore, the drying process may be preferably carried out at a temperature of about 150 to about 200° C., more preferably at a temperature of about 160 to about 180° C.

Meanwhile, the drying time may be about 20 to about 90 min in consideration of process efficiency, but it is not limited thereto.

The drying method in the drying step is not particularly limited if it has been generally used in the drying process of the hydrogel polymer. Specifically, the drying step may be carried out by the method of hot air provision, infrared radiation, microwave radiation, UV ray radiation, and the like. The moisture content of the polymer after the drying step may be about 0.1 to about 10 wt %.

Subsequently, the step of pulverizing the dried polymer obtained from the drying step is carried out.

The polymer powder obtained after the pulverization step may have a diameter of about 150 to about 850 µm. In order to pulverize the polymer into such diameter, a pin mill, a hammer mill, a screw mill, a roll mill, a disc mill, or a jog mill may be used as the pulverizer, but it is not limited thereto.

Further, in order to maintain the properties of the super absorbent polymer powder which is finally commercialized after the pulverization step, a separate process of classifying the polymer powders obtained after the pulverization according to the particle size may be carried out. Preferably, after classifying the polymer having a diameter of about 150 to about 850 µm, only the polymer powder may be subjected to the surface cross-linking reaction and finally commercialized.

On the other hand, the preparation method of a porous super absorbent polymer may further include a step of further cross-linking the surface of the base resin powder in the presence of a surface cross-linking agent to form a surface cross-linked layer.

Any surface cross-linking agent that has been used for preparing a super absorbent polymer can be used as the surface cross-linking agent for forming the surface cross-linked layer formed on the base resin powder and the second cross-linked polymer included therein, without limitation.

For more specific examples, at least one selected from the group consisting of ethylene glycol, 1,3-propandiol, 1,4-butanediol, 1,6-hexanediol, propylene glycol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, ethylene carbonate and propylene carbonate may be used.

The method of adding the surface cross-linking agent to the base resin powder is not particularly limited. For example, a method of adding and mixing the surface cross-linking agent and the base resin powder in a reactor, a method of spraying the surface cross-linking agent on the base resin powder, and a method of mixing the base resin powder and the surface cross-linking agent while continuously providing them to a continuously operating mixer may be used.

When the surface cross-linking agent is added thereto, water and methanol may be further mixed therewith. When water and methanol are added thereto, there is an advantage that the surface cross-linking agent can be evenly dispersed in the base resin powder. At this time, the amount of water and methanol per 100 parts by weight of the base resin powder may be controlled for the purposes of inducing a uniform dispersion of the surface cross-linking agent, preventing an agglomeration phenomenon, and optimizing the surface penetration depth of the cross-linking agent.

The surface cross-linking reaction may be carried out by heating the base resin powder to which the surface cross-linking agent is applied at about 160° C. or more for 20 min. Particularly, in order to obtain the super absorbent polymer satisfying the properties according to one embodiment properly, the surface cross-linking process may be carried out under the condition that the maximum reaction temperature is about 180 to 200° C. and the maximum reaction temperature is maintained for about 20 min or more, or for about 20 min to 1 hour. Furthermore, the heat-up time from the initiation temperature, for example, about 160° C. or more, or about 160 to 170° C., to the maximum reaction temperature may be controlled to be about 10 min or more, or about 10 min to 1 hour. The super absorbent polymer exhibiting better properties can be prepared by satisfying the above surface cross-linking conditions.

The heating means for the surface cross-linking reaction is not particularly limited. It is possible to provide a thermal media thereto or provide a heat source directly thereto. At this time, usable thermal media may be a heated fluid such as steam, hot air, hot oil, and the like, but the present invention is not limited thereto. Furthermore, the temperature of the thermal media provided thereto may be properly selected in consideration of the means of the thermal media, heating speed, and target temperature of heating. Meanwhile, an electric heater or a gas heater may be used as the heat source provided directly, but the present invention is not limited thereto.

According to another embodiment of the present disclosure, a porous super absorbent polymer prepared by the above-mentioned preparation method is provided. This porous super absorbent polymer includes a base resin powder including a cross-linked polymer of a water soluble ethylene-based unsaturated monomer containing acidic groups which are at least partially neutralized, and an inorganic filler contained in the cross-linked structure of the cross-linked polymer, wherein the base resin powder includes a plurality of pores having a diameter of a sub-micron (sub-µm) scale in the cross-linked structure, and an interconnected pore structure in the form of an open channel in which 90% or more of the pores are connected to each other.

As described above, the porous super absorbent polymer exhibits improved absorption rate and excellent absorption performance as it includes the interconnected pore structure in the form of an open channel in which a plurality of pores having a diameter of a micron scale or a nano scale are connected to each other. An example of the interconnected pore structure is shown in FIGS. 1 and 2.

As shown in FIGS. 1 and 2, in the pore structure, most of the pores (for example, 90% or more, 90 to 100%, or 90 to 95%) are connected to each other in the form of an open channel. Therefore, moisture can be absorbed by a capillary pressure inside the super absorbent polymer, and it can be directly conveyed through the open channel into the super absorbent polymer by convection rather than diffusion. For this reason, the super absorbent polymer of the embodiment can exhibit very fast absorption rate.

In addition, in the super absorbent polymer, each of the pores may have a maximum diameter of 5 to 500 µm, 20 to 400 µm, or 30 to 150 µm, and the base resin powder may have a pore volume fraction of 0.74 or more, or 0.75 to 0.9, defined as a ratio of the volume of the plurality of pores to the total volume.

The maximum diameter of the pores can be measured by observing the internal pore structure of the super absorbent polymer using an electron microscope. In addition, since it is difficult to directly measure the volume of the inside of the super absorbent polymer having an interconnected pore structure, the pore volume fraction can be calculated and confirmed by filling a certain amount of super absorbent polymer with isopropyl alcohol and measuring the volume thereof.

Accordingly, the super absorbent polymer of another embodiment may exhibit higher absorption rate and better absorption performance.

The super absorbent polymer may have, for example, centrifuge retention capacity (CRC) to a saline solution (0.9 wt % aqueous solution of sodium chloride) for 30 min of 26 to 35 g/g, and absorption rate to a saline solution (0.9 wt % aqueous solution of sodium chloride) of less than 55 sec, or 35 sec to 53 sec, which is excellent absorption performance and very fast absorption rate.

Herein, the centrifuge retention capacity (CRC) may be measured according to EDANA method WSP 241.2. More specifically, the centrifuge retention capacity can be calculated by the following Calculation Equation 1, after making the super absorbent polymer absorb the saline solution for 30 min:

$$CRC\ (g/g) = \{[W_2\ (g) - W_1\ (g)]/W_0\ (g)\} - 1 \quad \text{[Calculation Equation 1]}$$

In Calculation Equation 1, $W_0$ (g) is an initial weight (g) of the super absorbent polymer, $W_1$ (g) is a weight of the apparatus measured after dehydrating the same by using a centrifuge at 250 G for 3 min without using the super absorbent polymer, and $W_2$ (g) is a weight of the apparatus with the superabsorbent polymer measured after soaking the super absorbent polymer in a 0.9 wt % saline solution for 30 min at room temperature and dehydrating the same by using a centrifuge at 250 G for 3 min.

In addition, the absorption rate to a saline solution (0.9 wt % aqueous solution of sodium chloride) may be measured by a vortex removal time. For reference, the vortex removal time can be determined by, for example, adding the above super absorbent polymer to a saline solution (0.9 wt % NaCl solution) while stirring, free swelling the same, and then measuring the time until the vortex of the liquid generated by the stirring disappeared and a smooth surface is formed.

And, the super absorbent polymer of the embodiment may have a particle shape of spherical or amorphous having a diameter of about 150 to 850 µm. In addition, it may further include a surface cross-linked layer, which is formed on a surface of the base resin powder and further cross-linked from the cross-linked polymer by a medium of a surface cross-linking agent.

Advantageous Effects

According to the present disclosure, it is possible to provide a method for preparing a porous super absorbent polymer exhibiting excellent absorption performance together with improved absorption rate as having a novel pore structure which was not present in the conventional super absorbent polymer, and a porous super absorbent polymer prepared therefrom.

This super absorbent polymer can be suitably applied to various products such as sanitary materials requiring fast absorption rate.

BRIEF DESCRIPTION OF THE DRAWINGS

FIG. 1 is a SEM image showing the pore structure of the porous super absorbent polymer prepared in Example 1.

FIG. 2 is a SEM image showing the pore structure of the porous super absorbent polymer prepared in Example 4.

FIG. 3 is a SEM image showing the pore structure of the porous super absorbent polymer prepared in Comparative Example 1.

FIG. 4 is a SEM image showing the pore structure of the porous super absorbent polymer prepared in Comparative Example 2.

FIG. 5 is a SEM image showing the pore structure of the super absorbent polymer prepared in Comparative Example 3.

DETAILED DESCRIPTION OF THE EMBODIMENTS

Hereinafter, the present invention will be described in more detail with reference to examples. However, these examples are for illustrative purposes only, and the invention is not intended to be limited by these examples.

EXAMPLE 1

Preparation of Super Absorbent Polymer 35.83 g of acrylic acid, 1.07 g (1 part by weight based on 100 parts by weight of the monomer) of sodium dodecyl sulfate (HLB: 40, number average molecular weight: 288) as an anionic surfactant, 0.06 g (1600 ppm) of polyethylene glycol diacrylate (Mw=598) as a cross-linking agent, 57.94 g of 30% sodium hydroxide (NaOH), 2.2 g (10 parts by weight based on 100 parts by weight of the monomer) of a silica nano particle (30 wt % dispersion) having a diameter of 12 nm, 1.42 g of sodium persulfate (10 wt % solution), and 7.76 g of water were mixed to prepare a monomer composition having an acrylic acid monomer concentration of 33.7 wt % and a neutralization degree of 90 mol %.

Thereafter, the monomer composition was stirred with applying a shear force at 5000 rpm for 60 min using a mechanical mixer to perform foaming.

Subsequently, the monomer composition was added through a feeder consisting of a movable conveyor belt of a polymerization reactor, and subjected to thermal polymerization for 20 min to prepare a hydrogel polymer.

The hydrogel polymer was transferred to a cutter and cut to 0.2 cm. Here, the moisture content of the cut hydrogel polymer was 50 wt %.

Subsequently, the hydrogel polymer was dried with a hot air drier at 185° C. for 40 min, and the dried hydrogel polymer was pulverized with a pin mill pulverizer. And then, the polymer having a diameter less than about 150 μm and the polymer having a diameter of about 150 μm to 850 μm were classified by using a sieve.

After proceeding up to the above classification, a base resin powder was obtained. Then, 0.67 g of 1,3-propanediol as a surface cross-linking agent was added to 2.8 g of water and 3.5 g of methanol, and mixed to prepare a surface cross-linking solution. Thereafter, the surface cross-linking solution was sprayed onto the base resin powder, and stirred at room temperature so that the surface cross-linking solution was evenly distributed on the base resin powder. Subsequently, the base resin powder mixed with the surface cross-linking solution was put into the surface cross-linking reactor and subjected to the surface cross-linking reaction.

In this surface cross-linking reactor, the base resin powder was surface cross-linked at 185° C. for 90 min to prepare a super absorbent polymer of Example 1. After the surface cross-linking reaction, a porous super absorbent polymer of Example 1 having a particle size of 150 μm to 850 μm was prepared The pore structure of the porous super absorbent polymer of Example 1 was confirmed using a scanning electron microscope as shown in FIG. 1. For reference, the right image is an enlarged image of the left image. As shown in FIG. 1, it was confirmed that the porous super absorbent polymer of Example 1 includes a plurality of pores having a maximum diameter of 5 to 400 μm, and an interconnected pore structure in the form of an open channel in which 90% or more of the pores are connected to each other.

EXAMPLE 2

Preparation of Super Absorbent Polymer

A porous super absorbent polymer of Example 2 was prepared in the same manner as in Example 1 except that 1.07 g (3 parts by weight based on 100 parts by weight of the monomer) of sodium dodecanoate (HLB: 21, number average molecular weight: 222) was used as the anionic surfactant.

By observing the pore structure using a scanning electron microscope in the same manner as in Example 1, it was confirmed that the porous super absorbent polymer of Example 2 includes a plurality of pores having a maximum diameter of 5 to 500 μm, and an interconnected pore structure in the form of an open channel in which 90% or more of the pores are connected to each other.

EXAMPLE 3

Preparation of Super Absorbent Polymer

A porous super absorbent polymer of Example 3 was prepared in the same manner as in Example 1 except that 1.07 g of Hannong COP-140 (oleyl phosphate-based surfactant, number average molecular weight: 460) was used as the anionic surfactant.

By observing the pore structure using a scanning electron microscope in the same manner as in Example 1, it was confirmed that the porous super absorbent polymer of Example 3 includes a plurality of pores having a maximum diameter of 5 to 400 μm, and an interconnected pore structure in the form of an open channel in which 90% or more of the pores are connected to each other.

EXAMPLE 4

Preparation of Super Absorbent Polymer 35.83 g of acrylic acid, 1.07 g (1 part by weight based on 100 parts by weight of the monomer) of sodium dodecyl sulfate (HLB: 40, number average molecular weight: 288) as an anionic surfactant, 0.06 g (1600 ppm) of polyethylene glycol diacrylate (Mw=598) as a cross-linking agent, 50.84 g of 30% sodium hydroxide (NaOH), 2.2 g (10 parts by weight based on 100 parts by weight of the monomer) of a silica nano particle (30 wt % dispersion) having a diameter of 12 nm, 1.42 g of sodium persulfate (10 wt % solution), and 7.76 g of water were mixed to prepare a monomer composition having an acrylic acid monomer concentration of 36.1 wt % and a neutralization degree of 80 mol %.

A porous super absorbent polymer of Example 4 was prepared in the same manner as in Example 1 except that the above monomer composition was used.

The pore structure of the porous super absorbent polymer of Example 4 was confirmed using a scanning electron microscope as shown in FIG. 2. For reference, the right image is an enlarged image of the left image. As shown in FIG. 2, it was confirmed that the porous super absorbent polymer of Example 4 includes a plurality of pores having a maximum diameter of 5 to 400 μm, and an interconnected pore structure in the form of an open channel in which 90% or more of the pores are connected to each other.

COMPARATIVE EXAMPLE 1

Preparation of Super Absorbent Polymer 35.83 g of acrylic acid, 1.07 g (1 part by weight based on 100 parts by weight of the monomer) of sodium dodecyl sulfate (HLB: 40, number average molecular weight: 288) as an anionic surfactant, 0.06 g (1600 ppm) of polyethylene glycol diacrylate (Mw=598) as a cross-linking agent, 46.54 g of 30% sodium hydroxide (NaOH), 2.2 g (10 parts by weight based on 100 parts by weight of the monomer) of a silica nano particle (30 wt % dispersion) having a diameter of 12 nm, 1.42 g of sodium persulfate (10 wt % solution), and 7.76 g of water were mixed to prepare a monomer composition having an acrylic acid monomer concentration of 37.8 wt % and a neutralization degree of 75 mol %.

Thereafter, the monomer composition was stirred with applying a shear force at 5000 rpm for 60 min using a mechanical mixer to perform foaming.

Subsequently, the monomer composition was added through a feeder consisting of a movable conveyor belt of a polymerization reactor, and subjected to thermal polymerization for 20 min to prepare a hydrogel polymer.

The hydrogel polymer was transferred to a cutter and cut to 0.2 cm. Here, the moisture content of the cut hydrogel polymer was 50 wt %.

Subsequently, the hydrogel polymer was dried with a hot air drier at 185° C. for 40 min, and the dried hydrogel polymer was pulverized with a pin mill pulverizer. And then, the polymer having a diameter less than about 150 μm and the polymer having a diameter of about 150 μm to 850 μm were classified by using a sieve.

After proceeding up to the above classification, a base resin powder was obtained. Then, 0.67 g of 1,3-propanediol as a surface cross-linking agent was added to 2.8 g of water and 3.5 g of methanol, and mixed to prepare a surface cross-linking solution. Thereafter, the surface cross-linking solution was sprayed onto the base resin powder, and stirred at room temperature so that the surface cross-linking solution was evenly distributed on the base resin powder. Subsequently, the base resin powder mixed with the surface cross-linking solution was put into the surface cross-linking reactor and subjected to the surface cross-linking reaction.

In this surface cross-linking reactor, the base resin powder was surface cross-linked at 185° C. for 90 min to prepare a super absorbent polymer of Example 1. After the surface cross-linking reaction, a porous super absorbent polymer of Example 1 having a particle size of 150 μm to 850 μm was prepared by classifying with a standard mesh of ASTM standard.

The pore structure of the porous super absorbent polymer of Comparative Example 1 was confirmed using a scanning electron microscope as shown in FIG. 3. Referring to FIG. 3, it was confirmed that the porous super absorbent polymer of Comparative Example 1 has a plurality of pores, but these pores are formed in an independent form that they are not connected to each other, so that the polymer has a pore structure different from that of Examples.

COMPARATIVE EXAMPLE 2

Preparation of Super Absorbent Polymer

A porous super absorbent polymer of Comparative Example 2 was prepared in the same manner as in Comparative Example 1 except that 1.07 g of dioctyl sulfosuccinate sodium salt (HLB: 11) as the anionic surfactant and a monomer composition with a neutralization degree of 90 mol % were used.

The pore structure of the porous super absorbent polymer of Comparative Example 2 was confirmed using a scanning electron microscope as shown in FIG. 4. Referring to FIG. 4, it was confirmed that the porous super absorbent polymer of Comparative Example 2 has a plurality of pores, but these pores are formed in an independent form that they are not connected to each other, so that the polymer has a pore structure different from that of Examples.

COMPARATIVE EXAMPLE 3

Preparation of Super Absorbent Polymer

A super absorbent polymer of Comparative Example 3 was prepared in the same manner as in Example 1 except that the monomer composition was stirred with applying a shear force at 2000 rpm for 60 min using a mechanical mixer to perform foaming.

The pore structure of the super absorbent polymer of Comparative Example 3 was confirmed using a scanning electron microscope as shown in FIG. 5. Referring to FIG. 5, it was confirmed that the super absorbent polymer of Comparative Example 3 has a non-porous structure in which pores are hardly observed.

EXPERIMENTAL EXAMPLES

The properties of the super absorbent polymers of Examples and Comparative Examples were evaluated according to the following methods, and the measured property values are shown in the following Table 1.

(1) Pore Volume and Pore Volume Fraction 2.5 g of the base resin powder before surface cross-linking was filled in a 4 ml cylindrical column, and the internal pore volume was defined based on the volume occupied by isopropyl alcohol (IPA). The porosity (pore volume fraction) was confirmed by the result of the pore volume and the result of an electron microscope (×50) analysis.

(2) Centrifuge Retention Capacity (CRC)

For the super absorbent polymers of Examples and Comparative Examples, the centrifuge retention capacity (CRC) by absorption ratio under a non-loading condition was measured according to the EDANA (European Disposables and Nonwovens Association) method WSP 241.2.

That is, after inserting $W_0$ (g, about 0.2 g) of each polymer obtained in Examples and Comparative Examples uniformly in a nonwoven fabric envelope and sealing the same, it was soaked in a 0.9 wt % saline solution at room temperature. After 30 min, it was dehydrated by using a centrifuge at 250 G for 3 min, and the weight $W_2$ (g) of each envelope was measured. Further, after carrying out the same operation without using the polymer, the weight $W_1$ (g) of each envelope was measured.

CRC (g/g) was calculated by using the obtained weight values according to the following Calculation Equation 1, and the water retention capacity was confirmed.

$$\text{CRC (g/g)} = \{[W_2(g) - W_1(g)]/W_0(g)\} - 1 \quad \text{[Calculation Equation 1]}$$

In Calculation Equation 1, $W_0$ (g) is an initial weight (g) of the super absorbent polymer, $W_1$ (g) is a weight of the apparatus measured after dehydrating the same by using a centrifuge at 250 G for 3 min without using the super absorbent polymer, and $W_2$ (g) is a weight of the apparatus with the superabsorbent polymer measured after soaking the super absorbent polymer in a 0.9 wt % saline solution for 30 min at room temperature and dehydrating the same by using a centrifuge at 250 G for 3 min.

(3) Content of Water Soluble Component 1.0 g of a sample having a diameter of 300 μm to 500 μm of the super absorbent polymer prepared in Examples and Comparative Examples was placed in a 250 mL erlenmeyer flask, and free swollen in a 200 mL saline solution which is 0.9 wt % aqueous solution of sodium chloride while stirring at 250 rpm for 1 hour. Thereafter, the aqueous solution was filtered by a filter paper. The filtrate was primarily titrated to pH 10 with 0.1 N sodium hydroxide solution, and then back-titrated to pH 2.7 with 0.1 N hydrogen chloride solution. The content (wt %) of water soluble component in the super absorbent polymer was calculated from the obtained titration amount in accordance with EDANA WSP 270.3.

(4) Absorption Rate (s)

2.0 g of a sample having a diameter of 300 μm to 500 μm of the super absorbent polymer prepared in Examples and Comparative Examples was placed in a 100 mL flask. And then, it was added to 50 mL of a saline solution which is 0.9 wt % aqueous solution of sodium chloride, and free swollen while stirring at 600 rpm. Thereafter, the time was measured until the vortex of the liquid generated by the stirring disappeared and a smooth surface was formed.

The properties measured by the above methods are listed in Table 1.

TABLE 1

| | Pore volume (IPA, ml) | Pore volume fraction (whether it is 0.74 or more; SEM X50) | CRC (g/g) | Content of water soluble component (wt %) | Absorption rate (s) |
|---|---|---|---|---|---|
| Example 1 | 2.3 | ○ | 31.5 | 15.9 | 39 |
| Example 2 | 2.5 | ○ | 26.0 | 7.9 | 41 |
| Example 3 | 2.3 | ○ | 30.3 | 11.5 | 49 |
| Example 4 | 2.4 | ○ | 32.4 | 8.2 | 50 |
| Comp. Ex. 1 | 1.8 | X | 28.2 | 3.0 | 60 |
| Comp. Ex. 2 | 2.0 | X | 25.0 | 16.4 | 58 |
| Comp. Ex. 3 | 1.0 | X | 21.1 | 12.6 | 88 |

Referring to Table 1, it was confirmed that the super absorbent polymer of Examples exhibited the absorption performance (water retention capacity) at least equal to or higher than that of Comparative Examples and the absorption rate superior to that of Comparative Examples.

The invention claimed is:

1. A preparation method of a porous super absorbent polymer, comprising the steps of:
   preparing a monomer composition comprising a water soluble ethylene-based unsaturated monomer containing acidic groups which are at least partially neutralized, an internal cross-linking agent, an initiator, an inorganic filler, and an anionic surfactant;
   stirring the monomer composition under a shear force at a rate of 3000 to 20,000 rpm to generate bubbles in the monomer composition;
   preparing a hydrogel polymer by cross-linking the monomer composition; and
   preparing a base resin powder by drying, pulverizing, and classifying the hydrogel polymer,
   wherein the monomer has acidic groups which are at least 80 mol % neutralized, and
   the anionic surfactant has 10 or more carbon atoms or HLB of 15 or more, and includes a compound in the form of a sulfate salt, a carboxylate salt or a phosphate salt.

2. The preparation method of a porous super absorbent polymer of claim 1, wherein the anionic surfactant is used in an amount of 0.1 to 5 parts by weight based on 100 parts by weight of the monomer.

3. The preparation method of a porous super absorbent polymer of claim 1, wherein the anionic surfactant comprises sodium dodecyl sulfate, sodium dodecanoate, alkyl phosphate having a C10 to C30 alkyl group, alkyl sulfate having a C10 to C30 alkyl group, or alkyl carboxylate having a C10 to C30 alkyl group.

4. The preparation method of a porous super absorbent polymer of claim 1, wherein the anionic surfactant has a number average molecular weight of 220 to 800.

5. The preparation method of a porous super absorbent polymer of claim 1, wherein the step of stirring is carried out for 1 min to 100 min.

6. The preparation method of a porous super absorbent polymer of claim 1, wherein the water soluble ethylene-based unsaturated monomer comprises an anionic monomer of acrylic acid, methacrylic acid, maleic anhydride, fumalic acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, or a salt thereof.

7. The preparation method of a porous super absorbent polymer of claim 1, wherein the internal cross-linking agent comprises at least one selected from the group consisting of polyethylene glycol diacrylate (PEGDA), glycerine diacrylate, glycerine triacrylate, unmodified or ethoxylated trimethylol triacrylate (TMPTA), hexanediol diacrylate, and triethylene glycol diacrylate.

8. The preparation method of a porous super absorbent polymer of claim 1, wherein the inorganic filler comprises a silica nanoparticle or an alumina nanoparticle.

9. The preparation method of a porous super absorbent polymer of claim 1, further comprising a step of further cross-linking the surface of the base resin powder in the presence of a surface cross-linking agent to form a surface cross-linked layer.

10. The preparation method of a porous super absorbent polymer of claim 9, wherein the surface cross-linking agent comprises at least one selected from the group consisting of ethylene glycol, 1,3-propandiol, 1,4-butanediol, 1,6-hexanediol, propylene glycol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, ethylene carbonate and propylene carbonate.

11. A porous super absorbent polymer, comprising a base resin powder comprising a cross-linked polymer of a water soluble ethylene-based unsaturated monomer containing acidic groups which are at least partially neutralized, and an inorganic filler contained in the cross-linked structure of the cross-linked polymer, wherein the base resin powder comprises a plurality of pores having a diameter of a sub-micron (sub-μm) scale in the cross-linked structure, and an interconnected pore structure in the form of an open channel in which 90% or more of the pores are connected to each other.

12. The porous super absorbent polymer of claim 11, wherein each of the pores has a maximum diameter of 5 to 500 μm.

13. The porous super absorbent polymer of claim 11, wherein the base resin powder has a pore volume fraction of 0.74 or more, defined as a ratio of the volume of the plurality of pores to the total volume.

14. The porous super absorbent polymer of claim 11, wherein centrifuge retention capacity (CRC) to a saline solution (0.9 wt % aqueous solution of sodium chloride) for 30 min is 26 to 35 g/g, and absorption rate to a saline solution (0.9 wt % aqueous solution of sodium chloride) is less than 55 sec.

15. The porous super absorbent polymer of claim 11, further comprising a surface cross-linked layer, which is formed on a surface of the base resin powder and further cross-linked from the cross-linked polymer by a medium of a surface cross-linking agent.

* * * * *